(12) United States Patent
Cheon et al.

(10) Patent No.: US 9,611,965 B2
(45) Date of Patent: *Apr. 4, 2017

(54) COUPLING WITH AUTOMATIC SEAL

(71) Applicant: Koolance, Inc., Auburn, WA (US)

(72) Inventors: Peter Cheon, Auburn, WA (US);
AnKuk Song, AnYang (KR);
EungSoon Lee, AnYang (KR); Tim Hunting, Auburn, WA (US)

(73) Assignee: Koolance, Inc., Auburn, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/627,408

(22) Filed: Feb. 20, 2015

(65) Prior Publication Data

US 2016/0010777 A1 Jan. 14, 2016

Related U.S. Application Data

(63) Continuation of application No. 13/684,132, filed on Nov. 21, 2012, now Pat. No. 8,985,131, which is a
(Continued)

(51) Int. Cl.
*F16L 37/32* (2006.01)
*F16L 37/367* (2006.01)
*A61M 39/10* (2006.01)
*A61M 39/26* (2006.01)
*F16L 37/248* (2006.01)
*F16L 37/34* (2006.01)
*F16L 21/08* (2006.01)
(Continued)

(52) U.S. Cl.
CPC .......... *F16L 37/367* (2013.01); *A61M 39/10* (2013.01); *A61M 39/1011* (2013.01); *A61M 39/26* (2013.01); *F16L 21/08* (2013.01); *F16L 37/248* (2013.01); *F16L 37/2445* (2013.01); *F16L 37/34* (2013.01); *F16L 55/07* (2013.01); *A61M 39/12* (2013.01); *A61M 2039/1027* (2013.01); *Y10T 137/0318* (2015.04); *Y10T 137/87949* (2015.04); *Y10T 137/87957* (2015.04)

(58) Field of Classification Search
CPC ......... F16L 37/30; F16L 37/34; F16L 37/367; F16L 37/2445; F16L 55/07; F16L 21/08
USPC ....................................... 137/614.03, 614.04
See application file for complete search history.

(56) References Cited

U.S. PATENT DOCUMENTS 2,753,195 A * 7/1956 Palmer .................. F16L 37/088
137/614.03
6,082,401 A * 7/2000 Braun et al. ........ F16L 37/0841
137/614.03
(Continued)

*Primary Examiner* — Kevin Lee
(74) *Attorney, Agent, or Firm* — DWC Law Firm, P.S.; David Chen

(57) ABSTRACT

A conduit coupling can have a male portion and a female portion, with each portion having an internal biasing member. When the male portion is disconnected from the female portion, the internal biasing member in the male portion can cause a seal on a moveable plug to be biased against a lip of a stationary wall member to seal liquid from leaking out of the male portion. Also, the internal biasing member in the female portion can cause a lip of a moveable wall member to be biased against a seal that is connected to a stationary plug. Both the stationary plug and moveable plug can be connected to retaining portions by strips that are disposed away from an axis of the conduit coupling.

20 Claims, 15 Drawing Sheets

Related U.S. Application Data continuation-in-part of application No. 12/715,375, filed on Mar. 1, 2010, now abandoned, which is a continuation-in-part of application No. 11/772,206, filed on Jun. 30, 2007, now abandoned.

(51) Int. Cl.
*F16L 37/244* (2006.01)
*F16L 55/07* (2006.01)
*A61M 39/12* (2006.01)

(56) References Cited

U.S. PATENT DOCUMENTS

| | | | |
|---|---|---|---|
| 8,985,131 B2* | 3/2015 | Cheon et al. | F16L 37/367 137/1 |
| 9,082,712 B2* | 7/2015 | Sekiya | H01L 21/304 |

* cited by examiner

COUPLING WITH AUTOMATIC SEAL

RELATED APPLICATION (S)

This application is a continuation of U.S. patent application Ser. No. 13/684,132, filed Nov. 21, 2012 now U.S. Pat. No. 8,985,131, which is a continuation-in-part of U.S. patent application Ser. No. 12/715,375, filed Mar. 1, 2010, now abandoned, which is a continuation-in-part of U.S. patent application Ser. No. 11/772,206, filed Jun. 30, 2007, now abandoned, all of which are incorporated herein by reference in their entireties.

BACKGROUND

1. Field of the Disclosure

The present disclosure relates to couplings, and more particularly, to couplings having spring loaded sealing capabilities for use in liquid transport conduit systems.

2. Description of Related Art

Conduit systems for transporting fluid, such as, for example, flexible tube systems for transferring liquids, often include stand-alone couplings. There couplings allow users to, among other things, install, maintain or replace discrete and separate conduit sections.

A variety of such couplings are known in the art. For example, U.S. Pat. No. 5,104,158 to Meyer et al., discloses a quick connecting/disconnecting coupling, that includes a female and male coupling member, each having a flow path through which fluid can flow. The coupling has a quick connecting/disconnecting clip member that is slidably mounted on the female coupling member and slidable between a connecting position and a disconnecting position. Although the patent discloses a seal when the male and female coupling members are connected, there is no seal when they are disconnected. As such, pressurized fluid is free to leak from the coupling members when they are disconnected.

In the coupling discussed in U.S. Pat. No. 5,104,158, used to connect flexible tubes, automatic sealing is provided upon disconnection of the coupling to prevent discharge of fluids. However, the connection/disconnection mechanism is complicated, a biasing member is unprotected and exposed to external contact, and a release clip may introduce risk of accidental disconnection of the coupling, which could result in leaks. Additionally, residual liquid can leak from a coupling when it is intentionally disconnected.

BRIEF SUMMARY OF THE DISCLOSURE

Various embodiments of the present disclosure provide a conduit coupling for use with fluid conduits that comprise a male portion having a fluid passage and female portion having a fluid passage. The male portion can be connectable to the female portion, and releasably locked together by twisting the portions relative to one another to provide a unified fluid passage through the conduit coupling.

The male portion and female portion can each having an internal biasing member for providing an automatic seal when the portions are disconnected from one another. That is, the internal biasing members can push annular sealing members against walls within each of the male portion and female portion, to seal the respective portions from discharging fluid when they are disconnected.

For example, in some embodiments of the coupling of the present disclosure, a first portion (such as, for example, a male portion) of the coupling has a first biasing member positioned to bias a moveable channel member positioned within a first fluid chamber. The moveable channel member can have a first plug portion with a seal member connected to the first plug portion. A second portion (such as, for example, a female portion) of the coupling can have a second biasing member positioned to bias a moveable wall member. The moveable wall member can have a seal connected to an outer surface of the moveable wall member. When the first portion and the second portion are disconnected, the first biasing member biases the moveable channel member to a position such that the seal member connected to the first plug portion is aligned with a first interior wall. Also, the second biasing member biases the moveable wall member to a position such that the seal connected to the outer surface of the moveable wall member is compressed against a contact surface.

In some embodiments, the conduit coupling can have one or more non-linear tracks on the female portion for use in releasably and securely locking the female portion to the male portion. Corresponding lock members formed on the male portion, such as stubs, can be insertable into the tracks and moveable in a non-linear fashion within the tracks to lock the male portion in a connected position with the female portion.

DETAILED DESCRIPTION

In the following description, certain specific details are set forth in order to provide a thorough understanding of various embodiments of the disclosure. However, upon reviewing this disclosure, one skilled in the art will understand that the disclosure may be practiced without many of these details. In other instances, well-known structures related to tubes, conduits, springs and materials of construction have not been described in detail to avoid unnecessarily obscuring the descriptions of the embodiments of the disclosure.

In the present description, the terms "about" or "consisting essentially of," and their equivalents, mean±20% of the indicated range, value, or structure, unless otherwise indicated. It should be understood that the terms "a" and "an" as used herein refer to "one or more" of the enumerated components. The use of the alternative (e.g., "or") should be understood to mean either one, both, or any combination thereof of the alternatives. As used herein, the terms "include" and "comprise" are used synonymously, which terms and variants thereof are intended to be construed as non-limiting.

Figure 1:
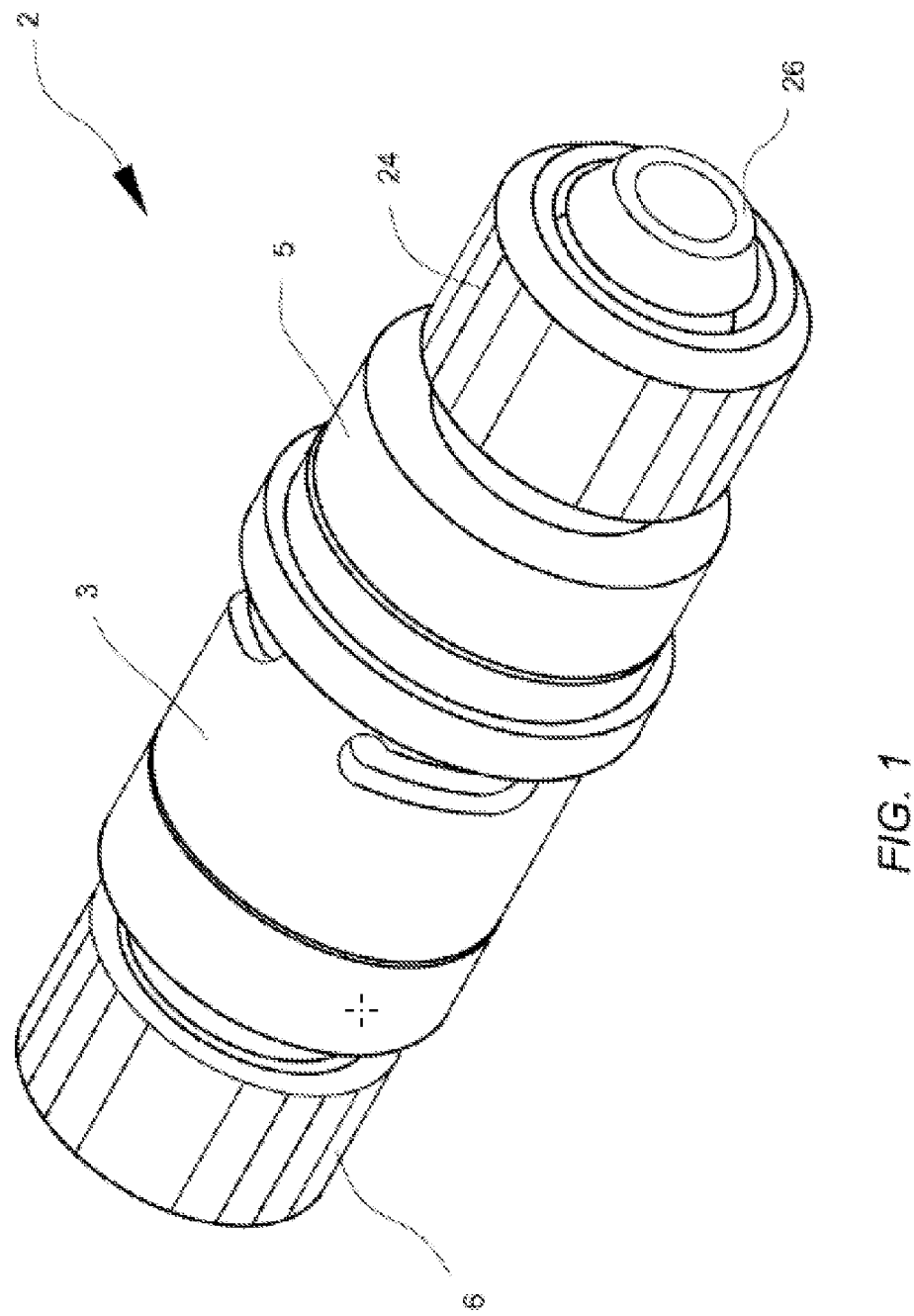
FIG. 1 is a perspective view of an embodiment of a coupling of the present disclosure.
Figure 2:
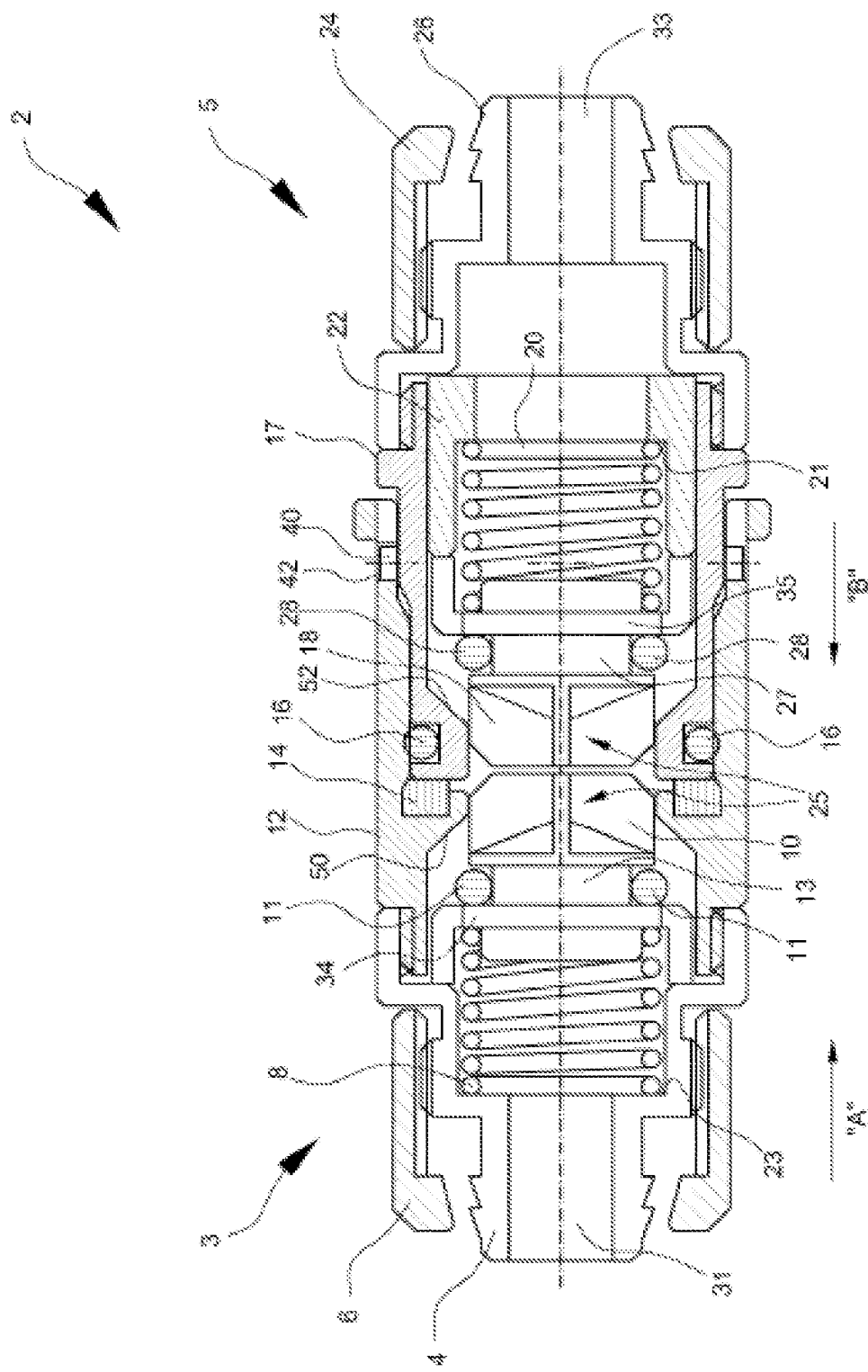
FIG. 2 is a cross sectional view of the coupling of FIG. 1, showing the male coupling portion and female coupling portion in a connected position.

FIG. 1 shows an embodiment of the coupling 2 of the present disclosure, having a female portion 3 and a male portion 5, with end caps 6, 24 and tube connector 26 on the male portion (a tube connector 4 is visible on the female portion in FIG. 2).

Figure 6:
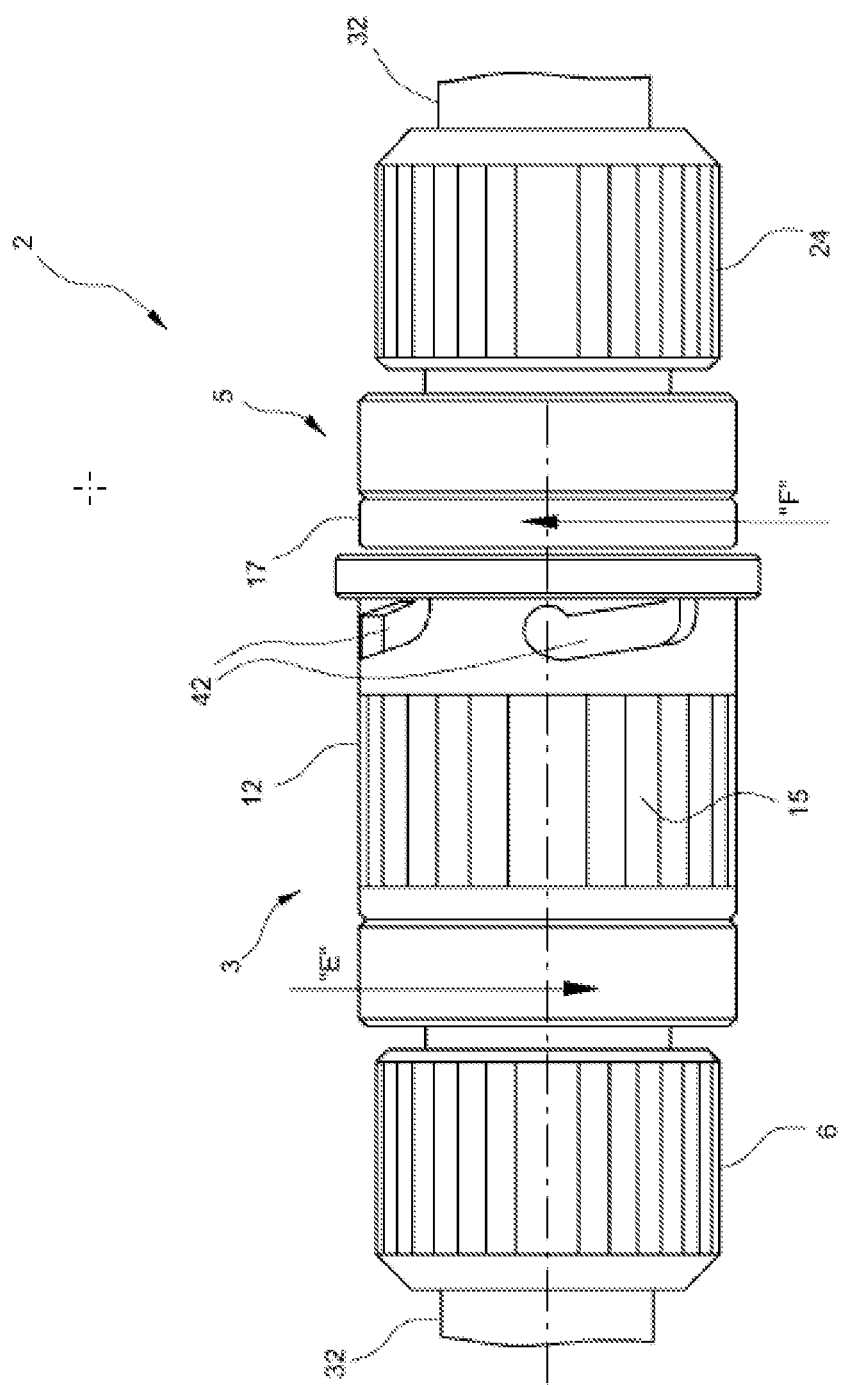
FIG. 6 is a side elevation view of the coupling of FIG. 1.

Referring to FIG. 6, conduit sections 32, such as flexible tube sections, can be sealably connected to the conduit coupling 2 and locked in place using end caps 6, 24.

Figure 3:
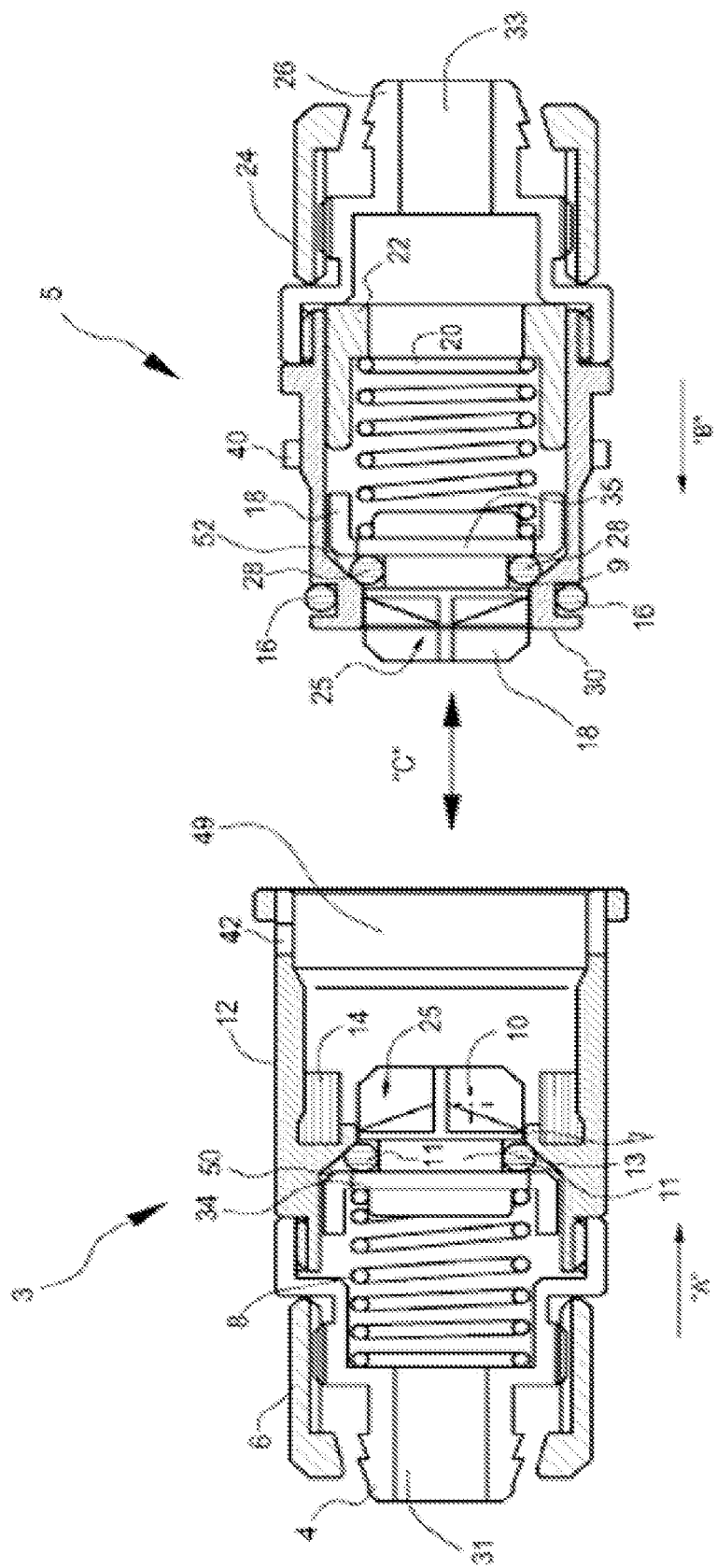
FIG. 3 is a cross sectional view of the coupling of FIG. 2, showing the male coupling portion and female coupling portion in a disconnected position.

Now referring to FIGS. 2 & 3, each of the coupling portions, female portion 3 and male portion 5, has an interior fluid channel that can pass over channel members (or valves) 10, 18 within the fluid channel, to allow fluid to flow through the coupling 2. Each of the coupling portions 3, 5 also has a biasing member 8, 20, which can be a coil spring in some embodiments of the present disclosure. The biasing members 8, 20 are set adjacent interior retaining walls 23, 21 of the respective female portion 3 and male portions 5, as can be seen in FIG. 2.

The biasing members 8, 20 provide biasing force against the channel members 10, 18 in the directions of arrows "A" and "B" respectively, and against annular seals 11, 28, which can be O-ring seals that circumferentially surround neck portions 13, 27 of the channel members 10, 18. As can be seen from FIGS. 2 & 4 in combination, the neck portions 13, 27 of the channel members 10, 18 can be circular.

As best seen in FIG. 3, showing the coupling 2 in a disconnected position, when the annular seals 11, 28 are freely biased in the direction of arrows "A" and "B' respectively, the annular seals 11, 28 are compressed against sealing walls 50, 52 of the female portion 3 and male portion 5, respectively. However, when an inward section 30 of the male portion 5 is manually inserted into a receiving chamber 49 of the female portion 3 in the direction of arrow "C," end portions of the channel members 10, 18 abut and apply force against the biasing members 8, 20 to cause each of the channel members 10, 18 to recede in an opposite direction from the approaching channel member. This, in turn, causes the annular seals 11, 28 to recede away from the sealing walls 50, 52 until they come to rest in their respective positions shown in FIG. 2. FIG. 2 is reflective of the connected position for the coupling 2.

As will be appreciated by one skilled in the art after reviewing this disclosure, the disconnected position shown in FIG. 3, provides an automatic seal via the compression of the annular seals 11, 28 against the sealing walls 50, 52. Fluid in the female portion 3 and male portion 5 of the coupling 2, which has entered into the coupling portions via fluid passage 31 or 33 (one of which is an entrance to the coupling 2, and one of which is an exit from the coupling 2, depending on direction of flow), is sealed from being discharged. As such, a sudden release of liquid from the coupling due to pressure drop from disconnecting the coupling and exposing it to atmospheric pressure, can be substantially prevented.

Figure 4:
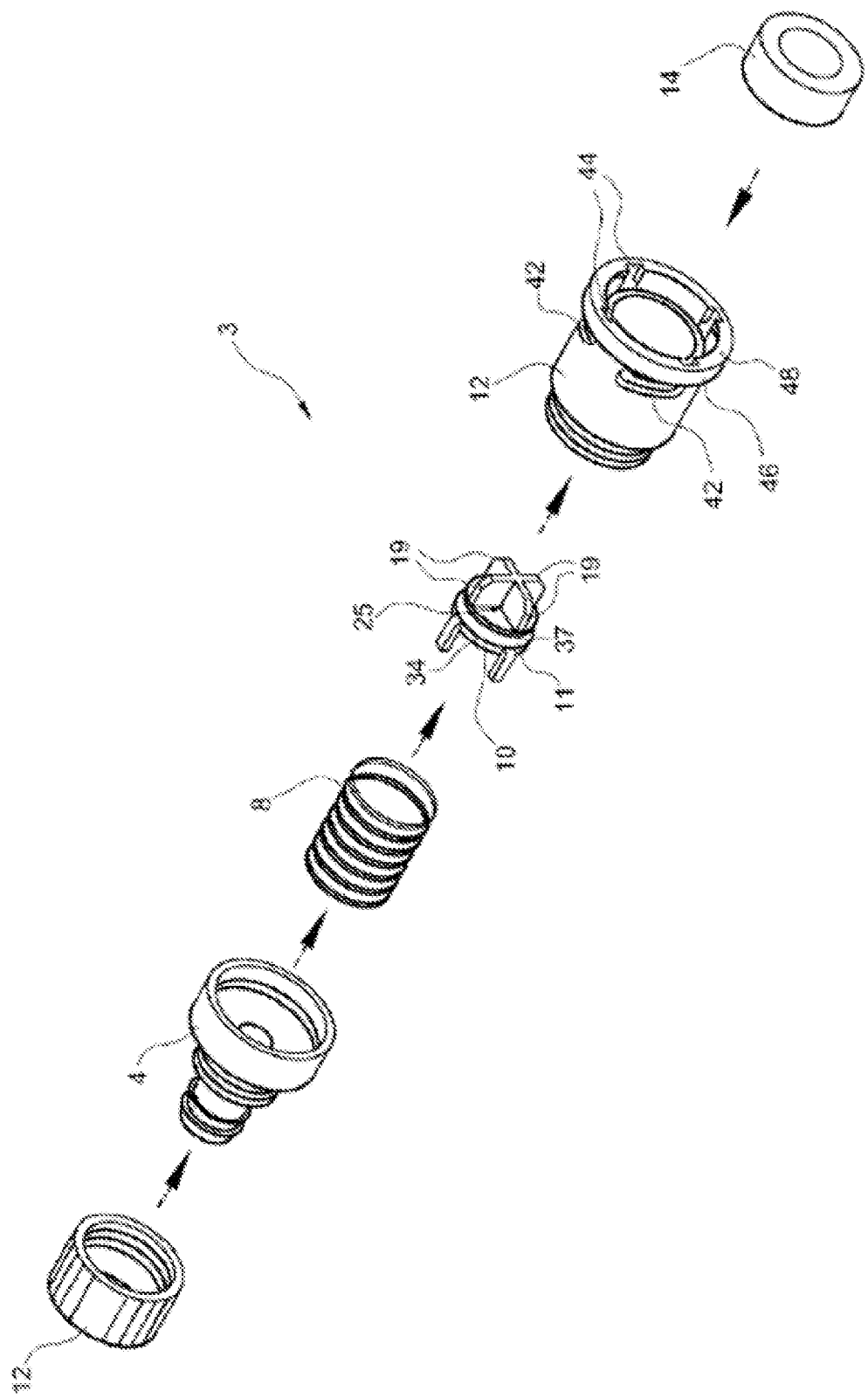
FIG. 4 is a perspective exploded view showing components of the female coupling portion of FIG. 1.

A releasable lock assembly can be provided for locking the female portion 3 to the male portion 5. First, referring to FIG. 4, the female portion 3 is provided with tracks 42 that extend through a wall of the female portion 3, near a flange 46. The tracks 42 also extend beneath a section of the flange 46, as best seen in FIG. 4. As such, track entrances 44 can be seen on the face 48 of the flange 46.

Figure 5:
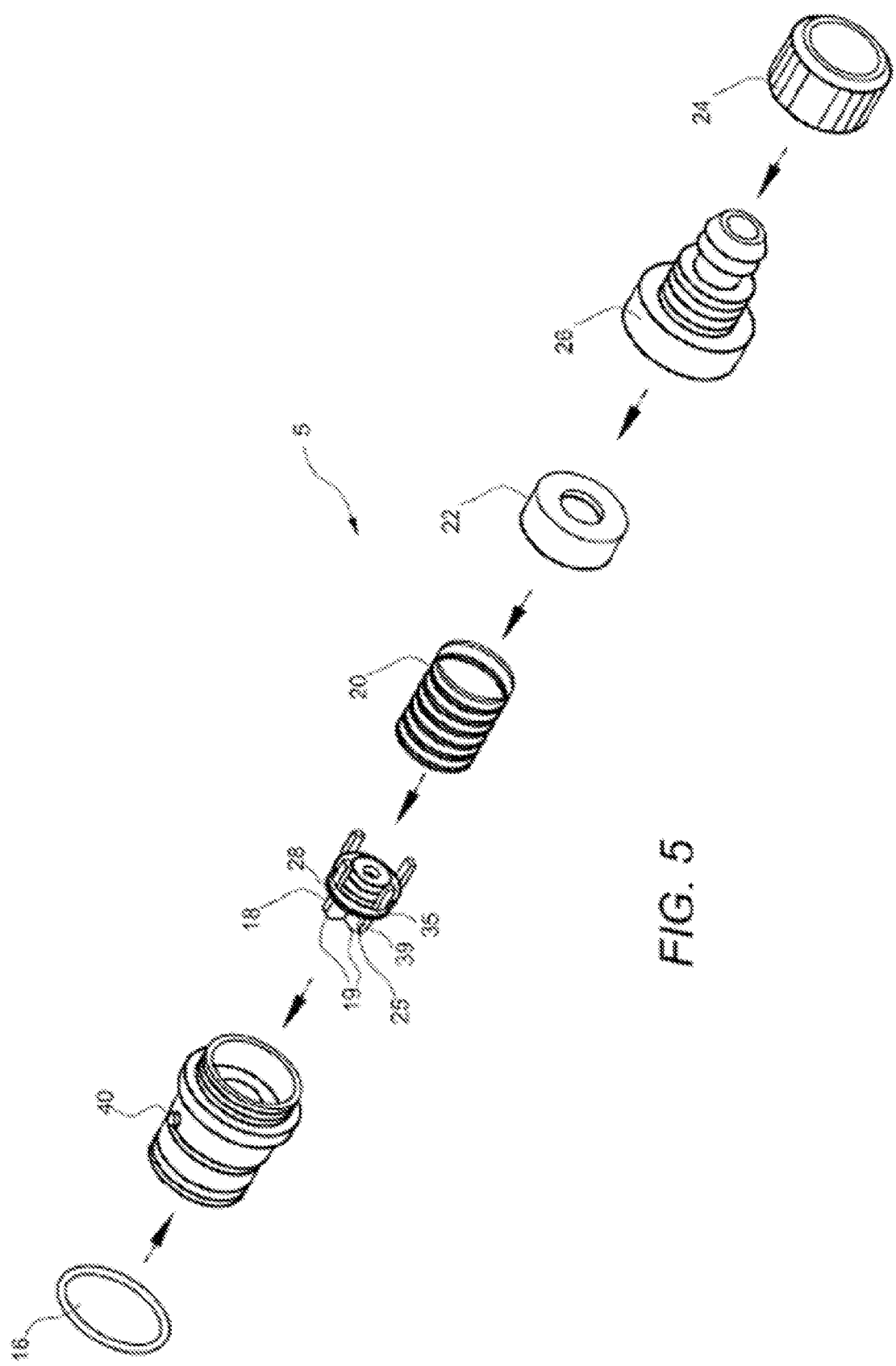
FIG. 5 is a perspective exploded view showing components of the male coupling portion of FIG. 1.

The tracks 42 are configured to receive stub members 40 of the male portion 5. A stub member 40 can be seen in FIG. 5. Multiple stub members 40 can be provided on the male portion 5 and multiple corresponding tracks 42 can be provided on the female portion 3, as will be appreciated by those skilled in the art after reviewing this disclosure.

Figure 7:
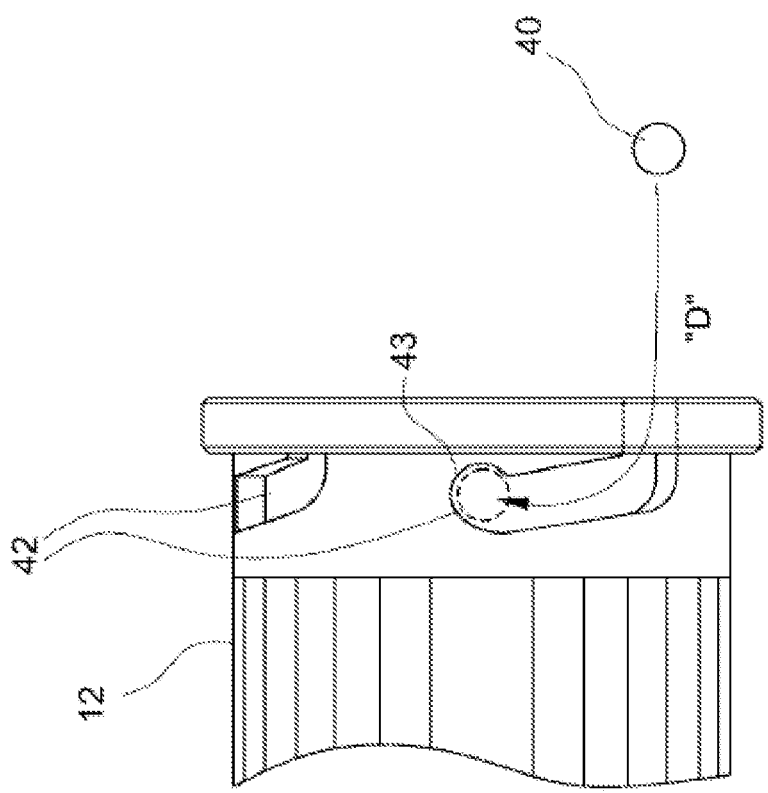
FIG. 7 is simplified side elevation view of the flange portion of the female coupling portion of FIG. 6, showing an interaction between a stub and a track of a releasable lock for the present disclosure.

When an inward section of the male portion 5 is inserted into the receiving chamber 49 of the female portion 3, one or more stub members 40 on the male portion 5 can be aligned with one or more corresponding track entrances 44, such that the stub members 40 can be pushed into the track 42, in the direction of arrow "D," as shown in FIG. 7. Arrow "D" moves forward into the track 42, then circumferentially across with respect to the surface of the female portion 3, then slightly back into a resting gap 43, to securely hold and releasably lock the male portion 5 in a connected position with the female portion 3. This can be accomplished by manually pushing the coupling portions 3, 5 together, then twisting them with respect to one another in the directions represented by arrows "E" and "F" shown in FIG. 6, then allowing the biasing members 8, 20 to bias the female and male portion away from each other slightly to push a stub members 40 back into the resting gaps 43. The coupling portions can be unlocked from one another by moving them in the opposite direction of arrow "D," to disconnect the female portion 3 and male portion 5 from one another. In some embodiments of the present disclosure, an outer grip member 15 is provided, which can be a grill-like surface to allow a user to grip the coupling 2 to turn it during locking and releasing.

When the female portion 3 and male portion 5 are in the connected position, as shown in FIG. 2, the annular seals 11, 28 are receded from the sealing walls 50, 52 respectively. Also, the channel members 10, 18 are receded inward into the respective female and male portions. As such, fluid can flow past the annular seals 11, 18 and past wedge gaps 25 of the channel members 10, 18. The wedge gaps 25 are formed between fins 19 (shown in FIGS. 4, 5) of the channel members 10, 28 and provide sufficiently large gaps for fluid to flow through to reduce pressure drop across the coupling 2. The fins 19 of each channel member 10, 18 can be planar walls aligned in parallel with a longitudinal axis of the conduit coupling 2, and can be connected to a circular wall 37, 39 of each channel member. When the conduit portions 3, 5 are disconnected, the channel members 10, 18 can be positioned such that their respective circular walls 37, 39 are substantially and snugly aligned with an opening of the respective sealing walls 50, 52. When the conduit portions 3, 5 are connected, the respective wedge gaps 25 of the channel members are aligned with the openings of the respective sealing walls 50, 52 to allow fluid to flow through the wedge gaps.

Furthermore, as can be seen in FIG. 2, when the coupling portions 3, 5 are connected, a sponge ring 14 of the female portion 3 is compressed against an inwardly facing wall of the male portion 5, and an annular connection seal 16 of the male portion 5 is compressed against an inside wall of the receiving chamber 49 of the female portion. As will be appreciated by those skilled in the art, the annular connection seal can prevent higher-pressure fluid inside the coupling 2 from leaking out of the coupling during use when the coupling is in a connected position. Also, the sponge ring 14 (also shown in FIGS. 3 & 4) can have absorbent characteristics, and can thus help absorb residual fluid in, for example, the receiving chamber 49 when the female portion 3 and male portion 5 are disconnected, thus further preventing fluid from spilling when the female and male portions are disconnected. The decompression of the sponge ring 14 when the female portion 3 is disconnected from the male portion 5 can allow the sponge ring to expand and absorb liquid.

Figure 8:
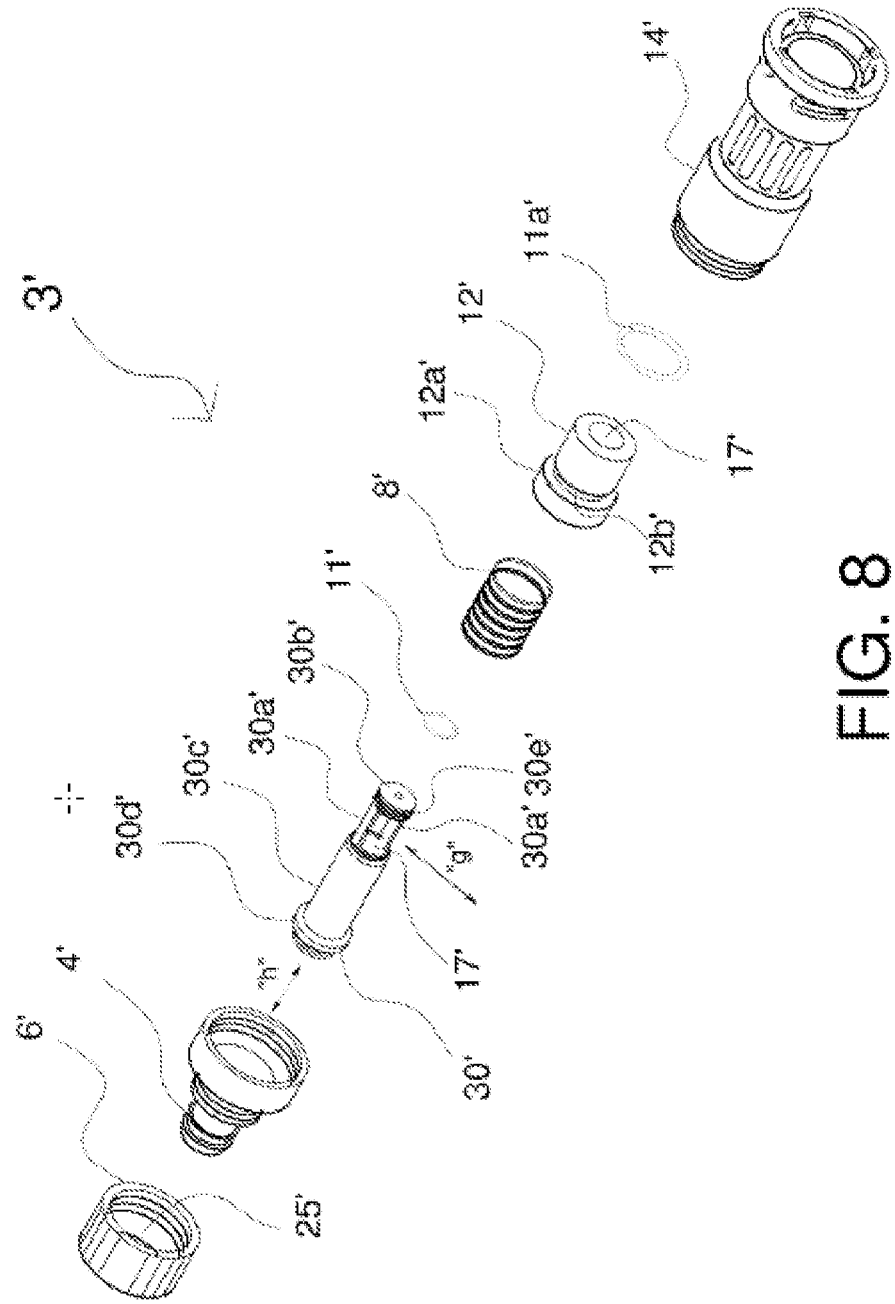
FIG. 8 is an exploded perspective view of a female portion of an alternative embodiment of a coupling of the present disclosure, the female portion being shown connected to a male portion of the coupling in FIG. 12.
Figure 10:
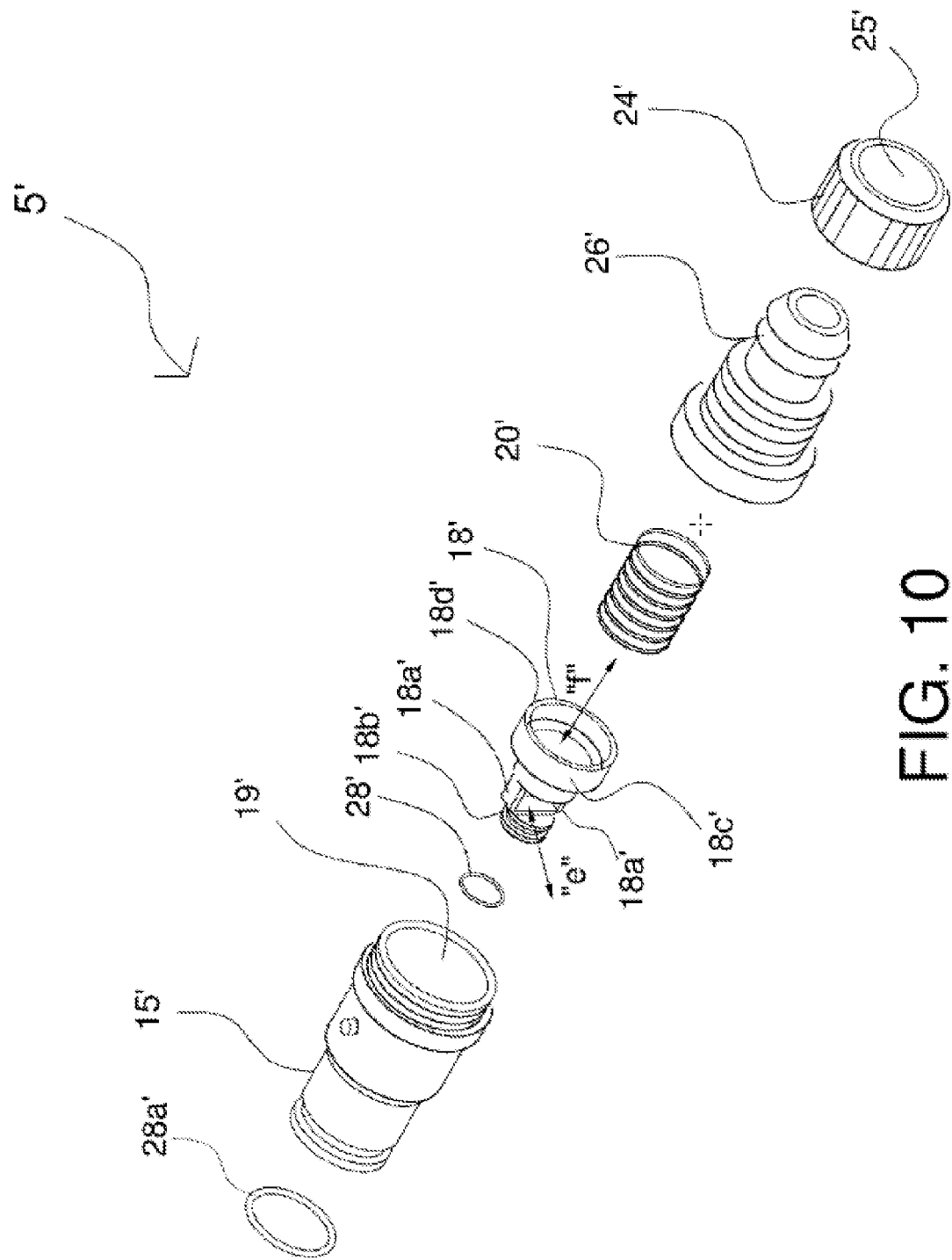
FIG. 10 is an exploded perspective view of a male portion of the coupling shown in FIG. 12.
Figure 12:
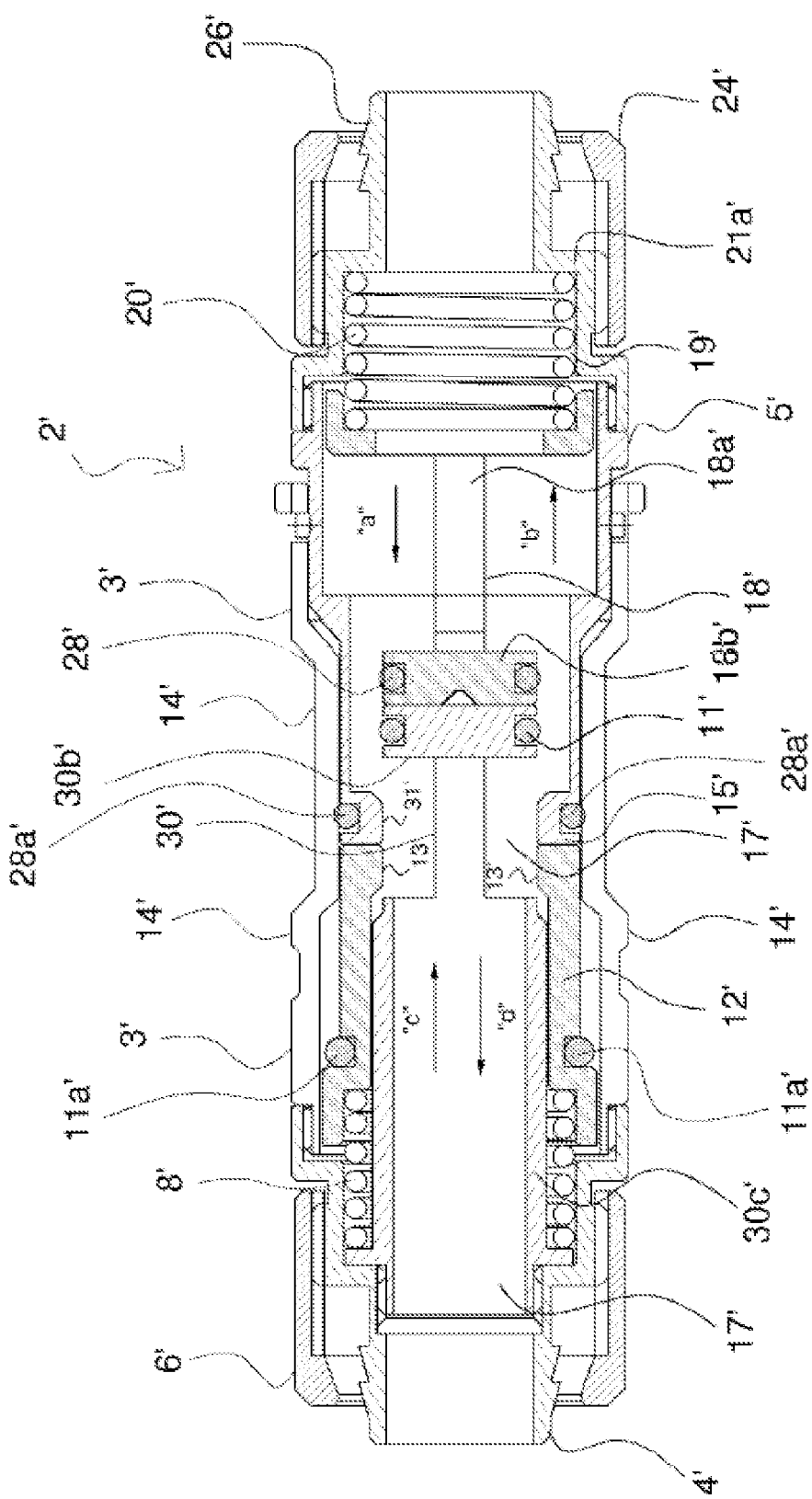
FIG. 12 is a side cross sectional view of an embodiment of a coupling of the present disclosure, showing the female portion of FIG. 8 connected to the male portion of FIG. 10.

Now, turning to another embodiment of the present disclosure, FIG. 12 illustrates another embodiment of the coupling 2' of the present disclosure, having a female portion 3' and a male portion 5'. FIGS. 8 & 10 show exploded views of embodiments of female portion 3' and male portion 5'. Each portion 3', 5' includes a respective tube connector 4' & 26' formed on an outside end of the portion. Each of the portions 3', 5' can include an end cap 6', 24' which is threadably attachable to the respective portion 3', 5'. Flexible tubes (not illustrated), or other types of fluid conduits in some embodiments, can be sealably connected to the each of the tube connectors 4' & 26' and, as best seen in FIGS. 8 & 10, the flexible tube sections (not illustrated) can be threaded through central holes 25' in the end caps 6', 24', and the end caps can be screwed onto end portions of the respective female portions 3' and male portion 5' to secure the tube sections to the tube connectors 4' & 26'.

Figure 11:
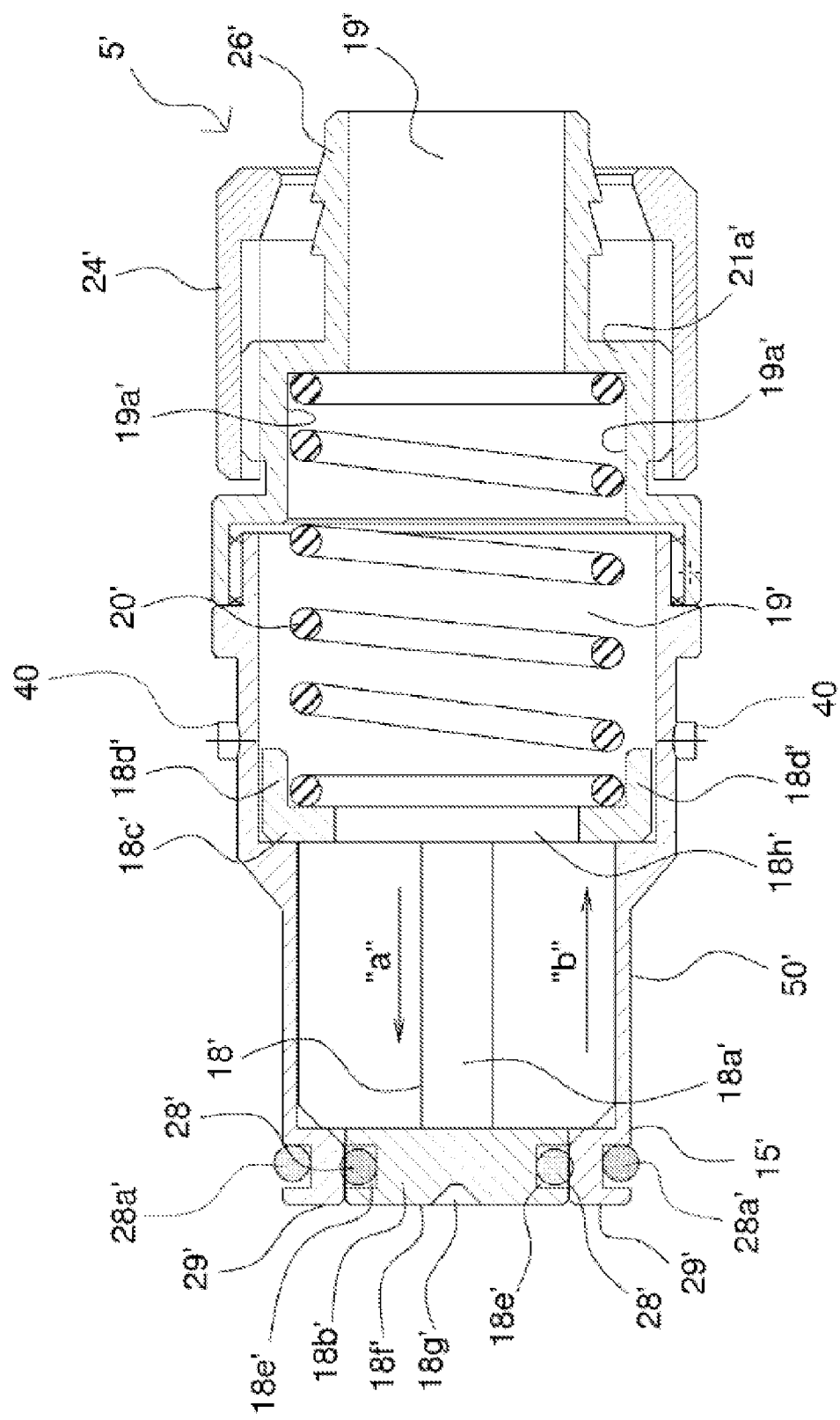
FIG. 11 is a side cross sectional view of the male portion of the coupling shown in FIG. 10.

Referring to FIGS. 10 & 11, the male portion 5' of conduit 2' has fluid chamber 19' which serves as an interior fluid channel. Fluid chamber 19' also contains first biasing member 20', and liquid can flow through the fluid chamber 19', including through an axial space of the first biasing member 20'. First biasing member 20' can be a coil spring which rests within the fluid chamber 19', with the fluid chamber 19' being cylindrical in shape. The outer circumferential edges of the coils of biasing member 20' can rest against the internal walls 19a' of the fluid chamber 19'.

A moveable channel member 18', to which a plug portion 18b' is attached, can be positioned within a portion of the fluid chamber 19'. The moveable channel member 18' includes a ring-like channel retainer 18c'. As best seen in FIG. 11, the channel retainer 18c' can be positioned adjacent the biasing member 20', with a circumferential wall 18d' (or outer wall) of the channel retainer 18c' extending in an axial (or longitudinal) direction of the fluid chamber 19' to surround an end portion of the biasing member 20', such that the outer circumferential edge of at least one coil of the biasing member 20' can rest against an interior surface of the circumferential wall 18d' of the channel retainer 18c'. Both the ring-like channel retainer 18c' and biasing member 20', which can be a coil spring, are disposed near outside perimeters of a flow path for fluid through the male portion 5'. An opposite end portion of the biasing member 20' can abut against a laterally extending retaining wall 21a', which is stationary to prevent movement of the biasing member 20' beyond the laterally extending retaining wall 21a'. As best seen in FIG. 10, the moveable channel member 18' can also include two or more extension strips 18a', which can be positioned on opposite sides of the moveable channel member 18' away from an axis of the ring-like channel retainer 18c', and which connect the channel retainer 18c' to the plug portion 18b' of the moveable channel member 18'. The channel strips 18a' allow fluid to flow through gaps between the strips 18a' to either exit from the gaps or enter into the gaps, as generally illustrated by arrow "e," and through a passageway 18h' of the moveable channel member 18' (See, FIG. 11), to enter or exit from an opposite end portion of the moveable channel member 18', as generally illustrated by arrow "f."

Referring to FIG. 11, the plug portion 18b' of the moveable channel member 18' includes an annular recess 18e' positioned on the outer sidewall thereof, within which can rest a first annular seal 28' (such as a seal ring). The annular seal 28' can be made of a compressible elastic material, such as, without limitation, an elastomer.

Figure 9:
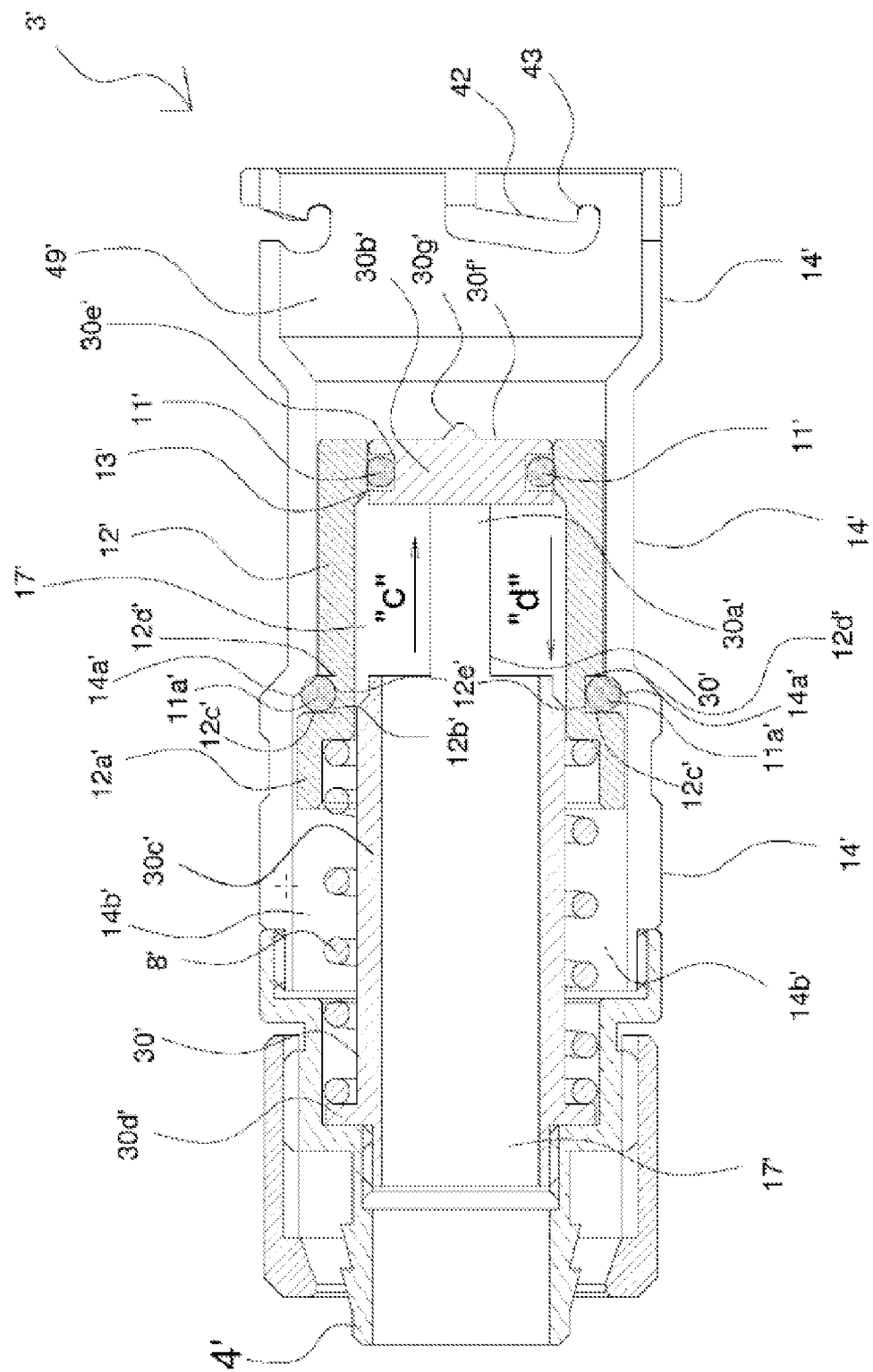
FIG. 9 is a side cross sectional view of the female portion of the coupling shown in FIG. 8.

Referring to FIGS. 8 & 9, the female portion 3' of conduit 2' has fluid chamber 17' which serves as the interior fluid channel. The inner wall surface of the fluid chamber 17' is comprised partly of the interior wall of a moveable wall member 12' and partly of the interior wall of a stationary channel member 30'. Both the moveable wall member 12' and stationary channel member 30' can be contained within an outer wall 14' of the female portion 3' of the coupling 2'. A hollow shaft 30c' of the stationary channel member 30' can be cylindrical with the interior of the shaft 30c' forming part of the fluid chamber 17'. A biasing member 8' (such as, for example, a coil spring) can be coiled about the shaft 30c' on an outside wall of the shaft 30c'. An first end portion of the biasing member 8' can abut against an outwardly extending annular flange 30d', formed on an outside wall of the shaft 30c', to prevent the biasing member 8' from slipping past the flange 30d'. ("Outwardly" in this context refers to a direction extending radially outward away from a central axis of the conduit coupling 2'). A second end portion of the biasing member 8' can be mated against a lateral surface of the moveable wall member 12' (which can be generally cylindrical in shape), within a cup portion 12a' of the moveable wall member 12', to bias the moveable wall member 12' toward the male portion 5' of the coupling 2', or inwardly ("Inwardly" in this context refers to a direction toward the other portion, such as the male portion 5', of the conduit coupling 2').

The stationary channel member 30' can include extension strips 30a', which connect the shaft 30c' to a plug portion 30b'. In the illustrated embodiments, there are two extension strips 30a', positioned on opposite sides of the stationary channel member 30' away from an axis of the stationary channel member 30' or the hollow shaft 30c', with the extension strips 30a' being generally aligned with a portion of the wall of the shaft 30c', as best seen in FIG. 8. Fluid can flow into, or out of, an outer end of the shaft 30c', as illustrated by arrow "h" in FIG. 8, and enter or exit the opposite end of the shaft 30c via gaps between the extension strips 30a, as illustrated by arrow "g" in FIG. 8.

The plug portion 30b' of the stationary channel member 30' includes an annular recess 30e' positioned on the outer sidewall thereof, within which can rest a second annular seal 11' (such as a seal ring). The second annular seal 11' can be made of a compressible elastic material, such as, without limitation, an elastomer.

Referring now to FIGS. 9, 11 & 12, in some embodiments of the present disclosure, an inward portion of the male portion 5' can be manually inserted into a receiving chamber 49' of the female portion 3'. The plug portion 30b' of the female portion 3', which is stationary with respect to the female portion, can abut against the plug portion 18b' of the male portion 5', which is moveable with respect to the male portion. Also, a lip 29' on the outer wall 15' of the male portion 5' which enters the receiving chamber 49' of the female portion 3' can abut against the moveable wall member 12' of the female portion 3'. As the female portion 3' and male portion 5' are pushed together, the plug portion 18b' of the male portion 5' is forced to move in the direction of arrow "b" (See FIG. 11) by being pushed by the stationary plug portion 30b' of the female portion and the moveable wall member 12' of the female portion 3' is forced to move in the direction of arrow "d" (See FIG. 9) by being pushed by the outer wall 15' of the male portion 5'. The beginning positions of the plug portion 18b' and the moveable wall member 12', before the male portion 5' and female portion 3' are connected, are shown in FIGS. 9 & 11, and the end positions of the plug portion 18b' and the moveable wall member 12', after the male portion 5' and female portion 3' are fully connected, are shown in FIG. 12. As can be seen in FIG. 12, the biasing members 8', 20' of the respective female and male portions, 3', 5', are thereby compressed through movement of the plug portion 18b' and moveable wall member 12'. The male portion 5' and female portion 3' can be removably locked together by a locking assembly, such as, for example, without limitation, the lock assembly described above for the embodiment of the coupling 2 shown in FIG. 1. That is, for example, the tracks 42 and resting gaps 43 can be provided on the female portion 3', as can be seen in FIG. 9, and the male portion 5' can have stubs 40, as can be seen in FIG. 11, suited for engaging the track 42 and resting gaps 43.

When the female portion 3' and male portion 5' are locked together, fluid can flow into one of the tube connectors 4', 26', through the fluid chambers 17', 19', and through gaps between the extension strips 30c', 18a', to pass through an opposite tube connector 4', 26'. The flow path is opened when the male portion 5' and female portion 3' are connected, in part, because the first annular seal 28', on the male portion 5', is displaced inward in the direction of arrow "b," as shown in FIGS. 11 & 12, away from being in contact and compressed against an inside wall 31' of an entrance lip 29' of the male portion 5', and, in part, because an interior contact wall 13' of the moveable wall member 12', is displaced in the direction of arrow "d," as shown in FIGS. 9 & 11, away from being in contact with and compressing the second annular seal 11'. Again, the displaced positions of the first annular seal 28' and interior contact wall 13' of the moveable wall member 12' are illustrated in FIG. 12, wherein the male portion 5' and female portion 3' are shown in a connected position.

It is also noted that, in some embodiments of the present disclosure, the forward facing surfaces of the respective plug portions 18b' and 30b', have flat portions 18f', 30f' (See, e.g., FIGS. 9 & 11) with the flat portions being in substantial parallel alignment with respect to one another. Also, a conically shaped recess 18g' is formed on the flat surface 18f' of the plug portion 18b' of the male portion 5', and laterally aligned with a conically shaped protrusion 30g' that is formed on the flat surface 30f' of the plug portion 30b' of the female portion 3'. When the female portion 3' is connected to the male portion 5', the flat portions 18f' & 30f' of the plug portions 18b' & 30b' are mated flush against one another, with the conically shaped protrusion 30g' fitting snugly within the conically shaped recess 18g'. This helps guide the plug portions during disconnection of the conduit 2' and leaves little or no room for fluid to be trapped between the plug portions 18b' & 30b' when the male portion 5 is disconnected from the female portion 3'. That is, as can be seen in FIG. 12, when the male portion 5' is being disconnected from the female portion 3', and the two portions are pulled apart from one another, the plug portions 18b' & 30b' stay flush with one another as plug portion 18b' is biased in the direction of arrow "a" by biasing member 20' and the moveable wall member 12' is biased in the direction of arrow "c" by biasing member 8'. Eventually, as the male portion 5' continues to be pulled apart from the female portion 3', the first annular seal 28' will come to be laterally aligned with and in contact with the inside wall 31' of entrance lip 29' to compress the seal 28', as shown in FIG. 11. Also, an interior contact wall 13' of the moveable wall member 12' will come to be longitudinally aligned and in contact with the second annular seal 11' to compress the seal 11', as shown in FIG. 9. Only then will biasing members 8', 20' be extended to the full extent permitted by the structural restrictions on the biasing members imposed by the female portion 3' and male portion 5', allowing the plug portions 18b' and 30b' to be separated from being flush against one another. This helps to ensure that no liquid has been trapped between the female portion 3' and male portion 5' to prevent leaking or spillage when the portions are disconnected for maintenance, conduit reconfiguration or disassembly, etc., as will be appreciated by those skilled in the art after reviewing this disclosure.

It is also noted that female portion 3' can comprise at least one other seal 11a' (e.g., annular seal member or seal ring), as shown in FIG. 9, which is retained on an outward end portion of a moveable wall member 12' within an annular recess 12b', the annular recess 12b' being located on a radially outer surface of the moveable wall member 12'. The annular recess 12b' is defined by two parallel facing lateral walls 12c' and 12d' and a bottom wall 12e'. Each of these walls, 12c', 12d', and 12e', extends about a circumferential perimeter of the moveable wall member 12'. The inwardly positioned lateral wall 12d' ("inwardly positioned" in this context means positioned closer inward toward the male portion 5') is shorter in radial length than the outwardly positioned lateral wall 12c'. As such, the outwardly positioned lateral wall 12c' extends radially outward away from a longitudinal axis of the female portion 3' further than, or is taller than, the inwardly positioned lateral wall 12d'. The annular seal member 11a' can be wedged between the inwardly positioned lateral wall 12d' and outwardly positioned lateral wall 12c'. The outer wall 14' of the female portion 3' includes an interior contact surface 14a' that extends radially and diagonally inward with respect to a longitudinal axis of the female portion 3, as shown in FIG. 9. A surface portion of the annular seal member 11a' is exposed above, or radially beyond, the inwardly positioned lateral wall 12d', as best seen in FIG. 9, so as to expose the surface portion of the annular seal member 11a' to the contact surface 14a'. That is, for example, when the female portion 3' is disconnect from the male portion 5', from the position shown in FIG. 12 to the position shown in FIG. 9, the moveable wall member 12' is pushed in the direction generally represented by arrow "c," by biasing member 8', until the exposed surface of the annular seal member 11a' is compressed against the contact surface 14a', as shown in FIG. 9. This restricts the moveable wall member 12' from being biased further toward the male portion 5' and seals any liquid within a chamber space 14b' between the hollow shaft 30c' and outer wall 14' that may be trapped in the chamber space.

It is noted that in the above described embodiments, the plug portions, such as plug portions 13b', 18b', are each longitudinally shorter than any of the extension strips, such as extension strip 18a', 30a', that connect them to the channel retainer 18c' or hollow shaft 30c', whereby, axial restriction of fluid flow is limited or reduced in comparison with systems that have longer relative obstructions at the axis of the flow path.

In some embodiments of the present disclosure, no tracks 42 or stub member 40, are provided for use in connecting the male portion 5 to the female portion 3. Instead, in some embodiments a female portion 3" can have an outer connection ring 60, as shown in FIGS. 13, 15-16, and 18. The outer connection ring 60 can float over the outer wall 14' of the female portion 3" of the coupling 2". A connection ring coil spring 64 can wrap about the outer wall 14', and sit concentrically within the connection ring 60. One end of the connection ring coil spring 64 (facing longitudinally away from the male portion 5") can abut against a laterally rising edge formed on the outer wall 14' of the female portion. The other end of the connection ring coil spring 64 can abut against a laterally inward extending edge of the connection ring 60 so as to place biasing force on the connection ring 60 when it is push longitudinally outward away from the male portion 5".

Figure 14:
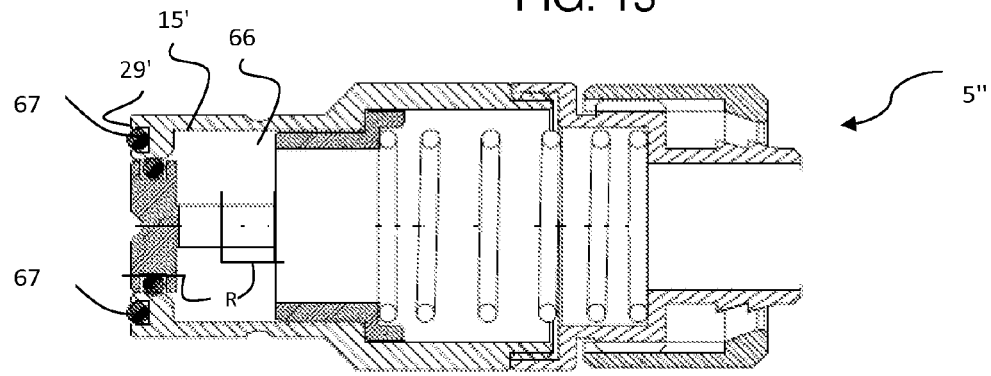
FIG. 14 is a side cross sectional view of another embodiment of a female portion of a coupling for the present disclosure.
Figure 15:
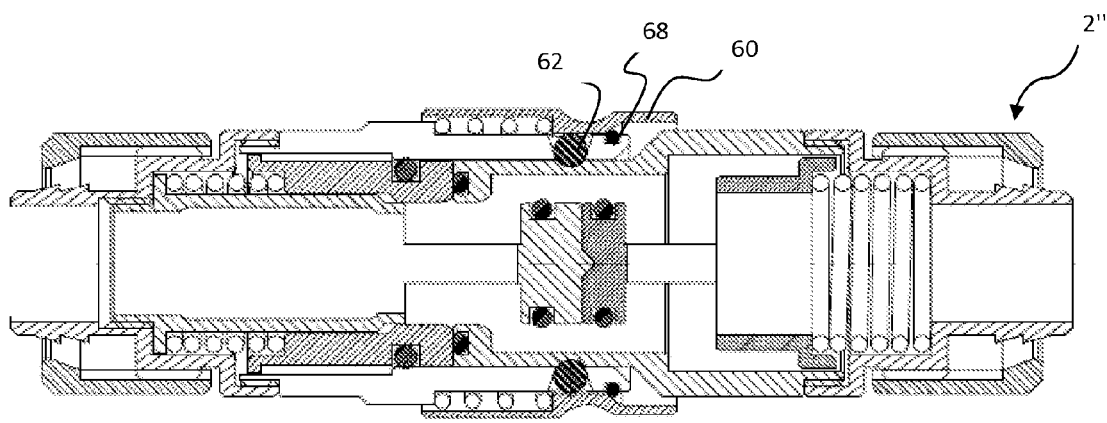
FIG. 15 is a side cross sectional view of the male portion and female portions of FIGS. 13 & 14 in a connected position.
Figure 16:
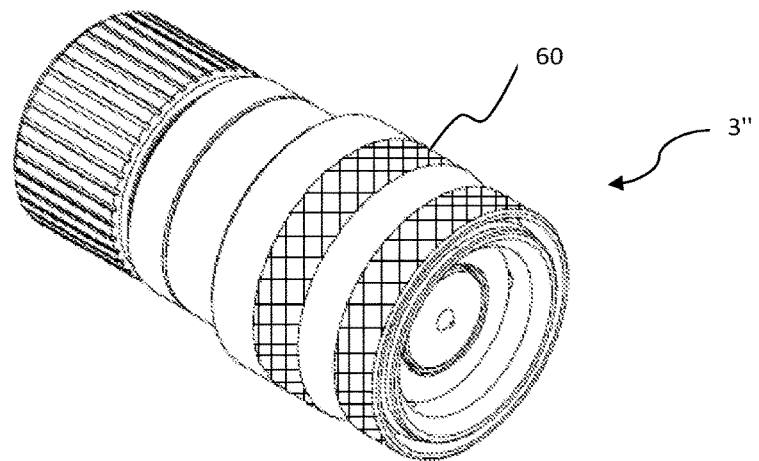
FIG. 16 is a perspective view of the male portion of FIG. 13.
Figure 17:
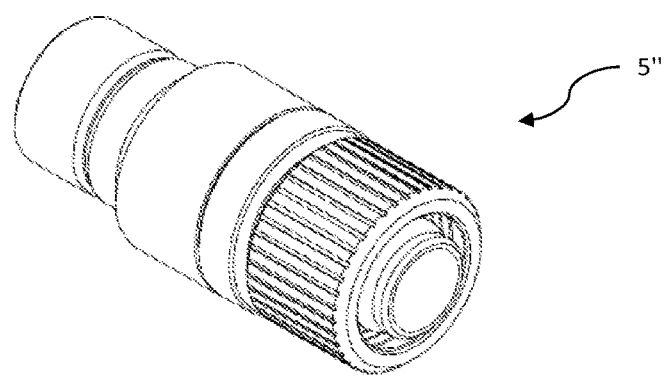
FIG. 17 is a perspective view of the female portion of FIG. 14.
Figure 18:
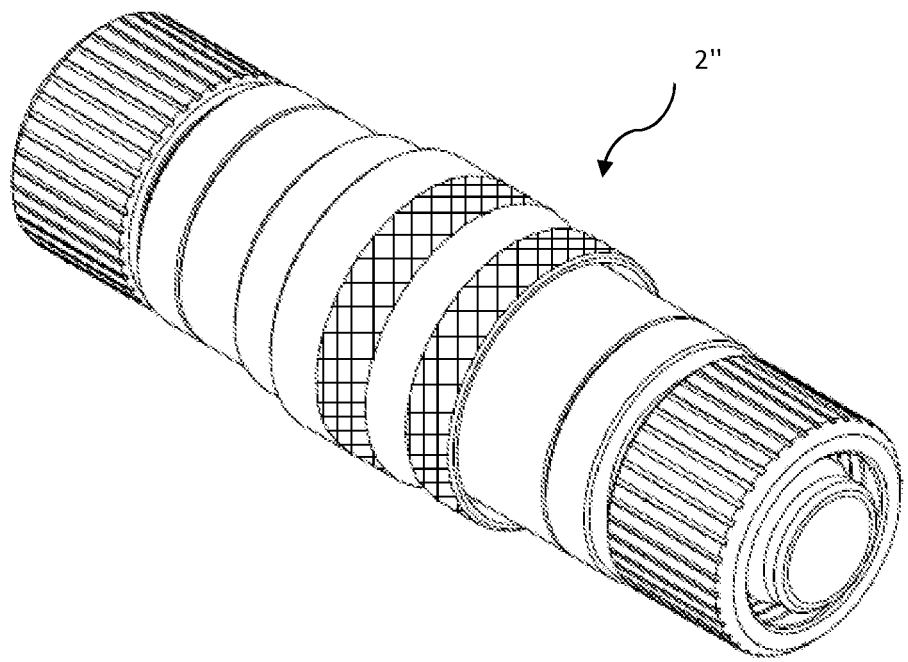
FIG. 18 is a perspective of the coupling of FIG. 15.

Referring to FIGS. 14, 15 & 17, in some embodiments, a male portion 5" includes an o-ring seal 67 disposed on an inward facing edge of the entrance lip 29' of the male portion 5". Also, an outer wall 15' of the male portion 5", on which the entrance lip 29' is positioned, can have an recessed annular groove 66. The cross-sectional contour of the annular groove 66, as shown in FIG. 14, can approximate a partial circle, so as to accommodate inward portions of a plurality of ball bearing 62 (discussed further below).

In some embodiments of the present disclosure, the female portion 3" includes a plurality of ball bearings 62, disposed beneath the connection ring 60. The ball bearings 62 can rest partially within a gap 72 provided on wall of the female portion 3". In a disconnected position, the moveable wall member 12' abuts against laterally inward surfaces of the ball bearing 62, to lift them upward toward an inward facing surface of the connection ring 60. When the connection ring 60 is pushed longitudinally outward away from the male portion 5", an laterally lower surface of the connection ring 60 can be pushed past the ball bearings 62, to allow the ball bearings 62 to rise laterally outward past a lower portion of a laterally outwardly extending wall 68 of the connection ring 68, and thereafter, the connection ring coil spring 64 can bias the laterally outwardly extending wall 68 against the ball bearings 62. When the male portion 3" is inserted into the female portion 3", the moveable wall member 12' is pushed back by the lip 29' and outer wall 15' of the male portion 5", until inward portions of the ball bearings 62 fall into the annular groove 66 of the male portion 5". This then drops allows the ball bearing 62 to drop out of the way of the laterally outwardly extending wall 68 (which can be slanted) on the connection ring 60, to allow the connection ring to be pushed longitudinally inward toward the male portion 5" by the connection ring coil spring 64, as best seen in FIG. 15. In this manner, the male portion 5" and female portion 3", can be removably stabilized in a connected position by the ball bearings 62, which extend both into the annular groove 66 and gap 72. When it is desired to disconnect the male portion 5" from the female portion 3", a user can push the connection ring 60 longitudinally outward away from the male portion 5", to again, allow the ball bearings 62 to rise above the lower inside surface of the connection ring 60, thus allowing the ball bearings to roll away from the annular groove 66 and rise up above the lower surface of the laterally outwardly extending wall 68 so that the ball bearings no longer retain the male portion and female portion together.

Also, it is noted that the position of the o-ring seal 67 disposed on an inward facing edge can help prevent damage of the o-ring 67 during connection and disconnection.

In the various embodiments described wherein a connection ring 60 is provided, various internal mechanical structures described for other embodiments herein can be provided, unless expressly stated otherwise, as will be appreciated by those skilled in the art after reviewing this disclosure.

Figure 13:
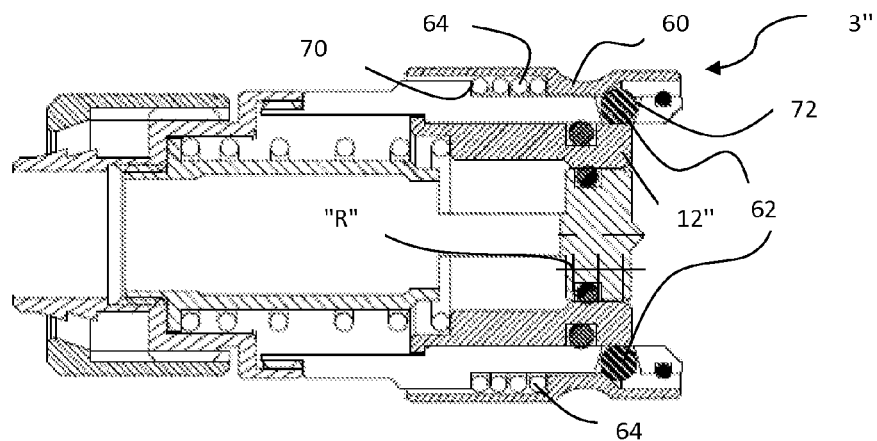
FIG. 13 is a side cross sectional view of another embodiment of a male portion of a coupling for the present disclosure.

It various embodiments described herein, the plug portions, such as plug portion 30b', 18b', are each be longitudinally shorter than about three to five times the diameter of a cross section of the o-ring seals attached to the plug portions, as shown in, for example, FIGS. 8-15, and as expressly referred to by reference lines "R" in FIG. 13. In some embodiments, the plug portions are even short in comparison with the size of the seal. It various embodiments described herein, the plug portions, such as plug portions 30b', 18b', are each longitudinally shorter than extension strips 30a', 18a', such as being less than one half the length of the extension strips, as shown in, for example, FIGS. 8-15, and as expressly referred to by reference lines "R" in FIG. 14. In some embodiments, the plug portions are even shorter in comparison with the extension strips. This can help limit axial obstruction of flow since the plug portions are the only axial flow obstruction (in the longitudinal axis of the coupling 2") in various embodiments herein.

Although specific embodiments and examples of the disclosure have been described supra for illustrative purposes, various equivalent modifications can be made without departing from the spirit and scope of the disclosure, as will be recognized by those skilled in the relevant art after reviewing the present disclosure. The various embodiments described can be combined to provide further embodiments. The described devices and methods can omit some elements or acts, can add other elements or acts, or can combine the elements or execute the acts in a different order than that illustrated, to achieve various advantages of the disclosure. These and other changes can be made to the disclosure in light of the above detailed description.

In general, in the following claims, the terms used should not be construed to limit the claimed invention(s) to the specific embodiments disclosed in the specification. Accordingly, the scope of invention is determined entirely by the following claims.

What is claimed is:

1. A conduit coupling for a fluid comprising:
   a first portion having a first biasing member positioned to bias a moveable channel member positioned within a first fluid chamber, the moveable channel member including a first plug portion and a seal connected to the first plug portion, the moveable channel member also including a retainer with the first plug portion being connected to the retainer by at least a one elongated member that is disposed away from an axis of the retainer;
   a second portion having a second biasing member positioned to bias a moveable wall member, the moveable wall member having a seal connected to the moveable wall member, with a stationary hollow shaft disposed adjacent the moveable wall member, and a second plug portion connected to the stationary hollow shaft by at least another elongated member, the at least another elongated member being disposed away from an axis of the stationary hollow shaft and the second plug portion having a seal connected to the second plug portion; and the first portion being releasably connectable to the second portion.

2. The conduit coupling of claim 1 further comprising a lip on the first portion, the lip facing the movable wall member of the second portion when the first and second portions are connected.

3. The conduit coupling of claim 1 wherein the first biasing member is a first coil spring and the first coil spring is disposed concentrically within the retainer, and both the first coil spring and retainer are positioned at an outer perimeter of a flow path for fluid through the first portion, and wherein the at least one elongated member and at least another elongated member are strip-like elongated members.

4. The conduit coupling of claim 1 wherein the at least one elongated member, and at least another elongated member are strip-like elongated members, and wherein the at least one elongated member is aligned with a wall of the retainer.

5. The conduit coupling of claim 1 wherein the second biasing member is a second coil spring, with the stationary hollow shaft disposed concentrically within the second coil spring, such that the second coil spring is not in a fluid flow path through the second portion.

6. The conduit coupling of claim 1 wherein the only obstructions to fluid flow through a longitudinal axis of the conduit coupling are the first plug portion and second plug portion and wherein the first plug portion is shorter than half the length of the at least one elongated member, and the second plug portion is shorter than half the length of the at least another elongated member.

7. The conduit coupling of claim 1 wherein the first plug portion and second plug portion are each longitudinally shorter than the at least one elongated member and at least another elongated member, whereby, axial restriction of fluid flow is limited.

8. The conduit coupling of claim 1 wherein when the first portion is connected to the second portion, the first plug portion is in contact with a second plug portion, and wherein when the first portion is retracted from the second portion to disconnect the portions, the first plug portion stays in contact with a second plug portion until the seal connected to the first plug portion is aligned with a first interior wall and the seal on the second plug portion is aligned with a contact wall.

9. The conduit coupling of claim 1 wherein when the first plug portion is in contact with the second plug portion, a protrusion on the second plug portion is snugly fitted within a recess on the first plug portion.

10. A conduit coupling for a fluid comprising:
a male portion having a first fluid chamber;
a first biasing member disposed adjacent a wall of the first fluid chamber;
a moveable channel member disposed adjacent an end portion of the first biasing member;
a moveable plug portion connected to the moveable channel member;
a seal connected to the moveable plug portion;
a female portion releasably connectable to the male portion and including a second fluid chamber;
a stationary hollow shaft forming part of the second fluid chamber, the hollow shaft being disposed adjacent a second biasing member;
a stationary plug portion connected to the hollow shaft; and
a seal connected to the stationary plug portion.

11. The conduit coupling of claim 10 further comprising a moveable wall member disposed adjacent an end portion of the second biasing member, the moveable wall member being moveable relative to the stationary hollow shaft when biased by the second biasing member.

12. The conduit coupling of claim 11 further comprising an annular seal connected to an outer wall of the moveable wall member.

13. The conduit coupling of claim 10 wherein when the male portion is disconnected from the female portion, an annular seal connected to a wall of the moveable wall member remains compressed against a contact surface before and after the disconnection.

14. The conduit coupling of claim 10 wherein when the male portion is disconnected from the female portion, the moveable plug portion is biased to a position in which the seal connected to the moveable plug portion is in contact with an inside wall of an entrance lip of the male portion.

15. The conduit coupling of claim 10 wherein when the male portion is disconnected from the female portion, the moveable wall member is biased to a position such that an interior contact wall on the moveable wall member comes into contact with the seal positioned on the stationary plug portion.

16. The conduit coupling of claim 10 wherein when the male portion is connected to the female portion, the moveable plug portion and the stationary plug portion are in contact, and when the male portion is being retracted from the female portion, the moveable plug portion stays in contact with the stationary plug portion until the seal connected to the moveable plug portion becomes aligned with and compressed against a wall and a seal connected to the stationary plug portion becomes aligned with and compressed against a wall.

17. The conduit coupling of claim 10 wherein the moveable plug portion is connected by at least one strip member to the movable channel member, with the strip member being disposed outside of a longitudinal axis of the male portion.

18. The conduit coupling of claim 17 wherein the stationary plug portion is connected by at least one strip to the stationary hollow shaft, with the strip being disposed outside of a longitudinal axis of the female portion.

19. A method of containing fluid flow within a disconnectable conduit coupling, the method comprising:
compressing a first biasing member in a first coupling portion to connect the first coupling portion to a second coupling portion by pressing a stationary member of the second coupling portion against a moveable member of the first coupling portion;
compressing a second biasing member in the second coupling portion to connect the second coupling portion to the first coupling portion by pressing a surface of the first coupling portion against a moveable wall of the second coupling portion;
passing fluid through the disconnectable conduit coupling past at least one elongated extension member in each of the first coupling portion and second coupling portion, the at least one elongated extension member in the first coupling portion being disposed outside of a longitudinal axis of the first coupling portion, and the at least one elongated extension member in the second coupling portion disposed outside of a longitudinal axis of the second coupling portion, the elongated extension member connecting the moveable member to a moveable retainer, and the second elongated extension member connecting the stationary member to a stationary shaft; and disconnecting the second coupling portion from the first coupling portion, and maintaining contact between the moveable member and stationary member until a seal member is compressed against an inside wall of the first coupling portion and a second seal member is compressed against a contact wall of the moveable wall of the second coupling portion.

20. The method of claim 19 wherein a longitudinal length of the movable member or stationary member is shorter than about three to five times a diameter of a cross section of the seal member or second seal member.

\* \* \* \* \*